(12) United States Patent
Burton et al.

(10) Patent No.: US 10,226,319 B2
(45) Date of Patent: Mar. 12, 2019

(54) REMOVAL OF OCCLUDED ALKALI METAL CATIONS FROM MSE-FRAMEWORK TYPE MOLECULAR SIEVES

(71) Applicant: ExxonMobil Research and Engineering Company, Annandale, NJ (US)

(72) Inventors: Allen W. Burton, Stewartsville, NJ (US); Karl G. Strohmaier, Port Murray, NJ (US); Scott J. Weigel, Allentown, PA (US)

(73) Assignee: EXXONMOBIL RESEARCH AND ENGINEERING, Annandale, NJ (US)

( * ) Notice: Subject to any disclaimer, the term of this patent is extended or adjusted under 35 U.S.C. 154(b) by 0 days.

(21) Appl. No.: 15/882,353

(22) Filed: Jan. 29, 2018

(65) Prior Publication Data

US 2018/0161139 A1    Jun. 14, 2018

Related U.S. Application Data

(63) Continuation of application No. 14/865,019, filed on Sep. 25, 2015, now Pat. No. 9,896,344.
(Continued)

(51) Int. Cl.
*C01B 39/48* (2006.01)
*B01J 29/70* (2006.01)
(Continued)

(52) U.S. Cl.
CPC ...... *A61F 2/0045* (2013.01); *A61B 17/06109* (2013.01); *A61B 17/3403* (2013.01);
(Continued)

(58) Field of Classification Search
CPC ........ C01B 39/026; C01B 39/48; B01J 29/70; B01J 37/10; B01J 37/30; B01J 2229/24;
(Continued)

(56) References Cited

U.S. PATENT DOCUMENTS

| | | |
|---|---|---|
| 3,354,078 A | 11/1967 | Maile et al. |
| 5,330,945 A | 7/1994 | Beckmeyer et al. |

(Continued)

FOREIGN PATENT DOCUMENTS

| | | |
|---|---|---|
| EP | 0909579 A1 | 4/1999 |
| WO | 2007064808 A1 | 6/2007 |

(Continued)

OTHER PUBLICATIONS

Elangovan et al., "A comparative study of zeolites SSZ-33 and MCM-68 for hydrocarbon trap applications", Microporous and Mesoporous Materials, Nov. 26, 2006, pp. 210-215, vol. 96, iss. 1-3, Elsevier, ScienceDirect.
(Continued)

*Primary Examiner* — David M Brunsman
(74) *Attorney, Agent, or Firm* — Lisa K. Holthus; Amanda K. Norwood

(57) ABSTRACT

A method for reducing the level of occluded alkali metal cations from an MSE-framework type molecular sieve comprises either (a) contacting the molecular sieve with a solution containing ammonium ions at a temperature of at least about 50° C. to ammonium-exchange at least part of the occluded potassium ions or (b) contacting the molecular sieve with steam at a temperature of at least about 300° C. and then subjecting the steamed molecular sieve to ammonium exchange.

20 Claims, 1 Drawing Sheet

Related U.S. Application Data

(60) Provisional application No. 62/063,615, filed on Oct. 14, 2014, provisional application No. 62/141,351, filed on Apr. 1, 2015.

(51) Int. Cl.

| | | |
|---|---|---|
| *A61F 2/00* | (2006.01) | |
| *C01B 39/02* | (2006.01) | |
| *B01J 37/10* | (2006.01) | |
| *B01J 37/30* | (2006.01) | |
| *B01D 53/04* | (2006.01) | |
| *B01D 53/75* | (2006.01) | |
| *B01D 53/86* | (2006.01) | |
| *F01N 3/08* | (2006.01) | |
| *C01B 39/04* | (2006.01) | |
| *B01D 53/92* | (2006.01) | |
| *B01D 53/94* | (2006.01) | |
| *A61B 17/06* | (2006.01) | |
| *A61B 17/34* | (2006.01) | |
| *B01J 29/03* | (2006.01) | |
| *A61B 17/04* | (2006.01) | |
| *A61B 17/00* | (2006.01) | |
| *A61B 17/32* | (2006.01) | |

(52) U.S. Cl.
CPC .......... *A61B 17/3468* (2013.01); *B01D 53/04* (2013.01); *B01D 53/75* (2013.01); *B01D 53/86* (2013.01); *B01D 53/864* (2013.01); *B01D 53/927* (2013.01); *B01D 53/9486* (2013.01); *B01J 29/0308* (2013.01); *B01J 29/70* (2013.01); *B01J 37/10* (2013.01); *B01J 37/30* (2013.01); *C01B 39/026* (2013.01); *C01B 39/04* (2013.01); *C01B 39/48* (2013.01); *F01N 3/0807* (2013.01); *F01N 3/0814* (2013.01); *F01N 3/0835* (2013.01); *A61B 17/0482* (2013.01); *A61B 2017/00805* (2013.01); *A61B 2017/320056* (2013.01); *B01D 2253/10* (2013.01); *B01D 2253/1085* (2013.01); *B01D 2253/112* (2013.01); *B01D 2253/116* (2013.01); *B01D 2257/702* (2013.01); *B01J 2229/186* (2013.01); *B01J 2229/24* (2013.01); *B01J 2229/36* (2013.01); *B01J 2229/38* (2013.01); *Y02T 10/22* (2013.01)

(58) Field of Classification Search
CPC ................ B01J 2229/36; B01J 2229/38; B01J 2229/186
See application file for complete search history.

(56) References Cited

U.S. PATENT DOCUMENTS

| | | | |
|---|---|---|---|
| 5,744,103 | A | 4/1998 | Yamada et al. |
| 6,049,018 | A | 4/2000 | Calabro et al. |
| 7,198,711 | B1 | 4/2007 | Chester et al. |
| 7,858,059 | B2 | 12/2010 | Davis et al. |
| 7,922,997 | B2 | 4/2011 | Moscosco et al. |
| 7,981,273 | B2 | 7/2011 | Nicholas et al. |
| 7,982,081 | B2 | 7/2011 | Nicholas et al. |
| 7,982,082 | B1 | 7/2011 | Nicholas et al. |
| 8,022,262 | B1 | 9/2011 | Moscosco et al. |
| 8,025,863 | B2 | 9/2011 | Strohmaier et al. |
| 8,053,618 | B1 | 11/2011 | Moscosco et al. |
| 8,058,496 | B2 | 11/2011 | Bogdan et al. |
| 8,071,830 | B1 | 12/2011 | Nicholas et al. |
| 8,071,831 | B1 | 12/2011 | Bogdan et al. |
| 9,896,344 | B2 * | 2/2018 | Burton .................. B01D 53/04 |
| 2005/0166581 | A1 | 8/2005 | Davis et al. |
| 2009/0318696 | A1 | 12/2009 | Strohmaier et al. |
| 2012/0260628 | A1 | 10/2012 | Elangovan et al. |
| 2013/0095030 | A1 | 4/2013 | Burton |
| 2013/0115163 | A1 | 5/2013 | Weston et al. |

FOREIGN PATENT DOCUMENTS

| | | |
|---|---|---|
| WO | 2008083126 A2 | 7/2008 |
| WO | 2013055879 A1 | 4/2013 |
| WO | 2014077995 A1 | 5/2014 |

OTHER PUBLICATIONS

Lopez et al., "Screening of different zeolites and silicoaluminophosphates for the retention of propene under cold start conditions", Microporous and Mesoporous Materials, May 2010, pp. 239-247, vol. 130, iss. 1-3, Elsevier, ScienceDirect.

Park et al., "A fast and quantitative assay for developing zeolite-type hydrocarbon trap catalyst", Microporous and Mesoporous Materials, Apr. 19, 2007, pp. 264-270, vol. 101, iss. 1-2, Elsevier, ScienceDirect.

Yeon et al., "Adsorption and desorption characteristics of hydrocarbons in multi-layered hydrocarbon traps", Microporous and Mesoporous Materials, Mar. 1, 2009, pp. 349-355, vol. 119, iss. 1-3, Elsevier, ScienceDirect.

Lafyatis, et al., "Ambient temperature light-off for automobile emission control", Applied Catalysis B: Environmental, Sep. 21, 1988, pp. 123-135, vol. 18, iss. 1-2, ScienceDirect, Elsevier.

Elangovan, et al., "SSZ-33: A Promising Material for Use as a Hydrocarbon Trap", Journal of Physical Chemistry B, Aug. 10, 2004, pp. 13059-13061, vol. 108, iss. 35., ACS Publications.

Puertolas et al., "Recent Solutions for the Abatement of Hydrocarbon Emissions During the Cold Start of Light Vehicles", Recent Patents on Chemical Engineering, 2011, pp. 36-52, vol. 4, iss. 1, Bentham Science Publishers.

Wang et al., "Synthesis of MAZ/ZSM-5 composite zeolite and its catalytic performance in FCC gasoline aromatization", Catalysis Communications, Jul. 1, 2007, pp. 1161-1166, vol. 8, No. 7, Elsevier Science, Amsterdam.

Shibata et al., "Synthetic investigation on MCM-68 zeolite with MSE topology and its application for shape-selective alkylation of biphenyl", Microporous and Mesoporous Materials, Dec. 1, 2008, pp. 216-226, vol. 116, No. 1-3, Elsevier Science, New York.

PCT/US2015/052125 Partial International Search Report dated Jan. 5, 2016.

PCT/US2015/052124 International Search Report and Written Opinion dated Jan. 7, 2016.

Dorset, et al., "Crystal Structure of Zeolite MCM-68: A New Three-Dimensional Framework with Large Pores", Journal of Physical Chemistry B, Jan. 6, 2006, pp. 2045-2050, vol. 110, iss. 5, ACS Publications.

Parikh et al., "Non-thermal calcination by ultraviolet irradiation in the synthesis of microporous materials", Microporous and Mesoporous Materials, Oct. 6, 2004, pp. 17-22, vol. 76, Elsevier, ScienceDirect.

* cited by examiner

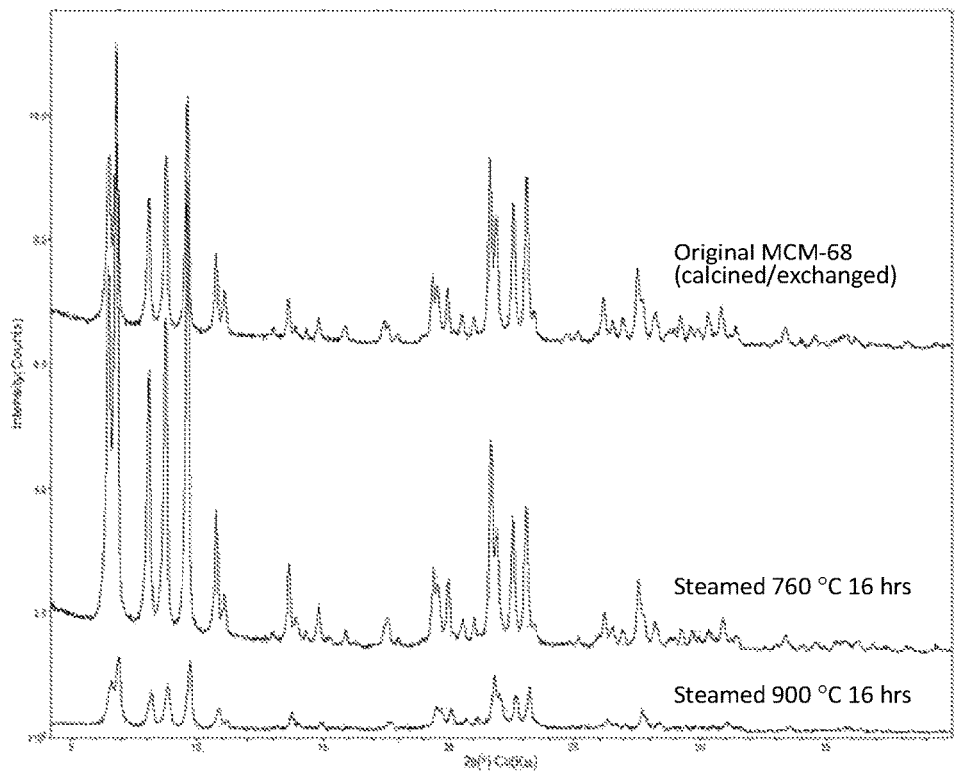

REMOVAL OF OCCLUDED ALKALI METAL CATIONS FROM MSE-FRAMEWORK TYPE MOLECULAR SIEVES

CROSS-REFERENCE TO RELATED APPLICATIONS

This application claims the benefit of U.S. patent application Ser. No. 14/865,019, filed Sep. 25, 2015; now U.S. Pat. No. 9,896,344; which claims benefit of provisional U.S. Ser. Nos. 62/063,615, filed Oct. 14, 2014, and 62/141,351, filed Apr. 1, 2015, the entire contents of each of which are expressly incorporated by reference herein.

This application is also related to the U.S. non-provisional application claiming priority to provisional U.S. Ser. No. 62/141,351, which is being filed on even date herewith.

FIELD OF THE INVENTION

This invention relates to the removal of occluded alkali metal cations from MSE-framework type molecular sieves, such as MCM-68.

BACKGROUND

Molecular sieves are classified by the Structure Commission of the International Zeolite Association according to the rules of the IUPAC Commission on Zeolite Nomenclature. According to this classification, framework-type zeolites and other crystalline microporous molecular sieves, for which a structure has been established, are assigned a three letter code and are described in the Atlas of Zeolite Framework Types, 6th edition, Elsevier, London, England (2007). MCM-68 is one of the molecular sieves for which a structure has been established and materials of this framework type are designated as MSE.

MSE framework-type molecular sieves have a 3-dimensional channel structure comprising one 12-membered ring channel system and two 10-membered ring channel systems, in which the channels of each system extend perpendicular to the channels of the other systems and in which the 12-ring channels are generally straight and the 10-ring channels are tortuous (sinusoidal).

The composition and characterizing X-ray diffraction pattern of MCM-68 are disclosed in U.S. Pat. No. 6,049,018, which also describes the synthesis of the molecular sieve in the presence of a structure directing agent comprising N,N,N',N'-tetraethylbicyclo-[2.2.2]oct-7-ene-2,3:5,6-dipyrrolidinium dications and/or N,N,N',N'-tetraalkylbicyclo-[2.2.2] octane-2,3:5,6-dipyrrolidinium dications. The entire contents of U.S. Pat. No. 6,049,018 are incorporated herein by reference.

U.S. Pat. No. 8,025,863 discloses that MSE framework-type molecular sieves can be synthesized using a structure directing agent selected from 1,1-dialkyl-4-cyclohexyl-piperazin-1-ium cations, 1,1-dialkyl-4-alkylcyclohexylpiperazin-1-ium cations and mixtures thereof. The entire contents of U.S. Pat. No. 8,025,863 are incorporated herein by reference.

U.S. Patent Application Publication No. 2013/0095030 discloses that MSE framework-type molecular sieves can be synthesized using a structure directing agent having one or both of the two following general structures:

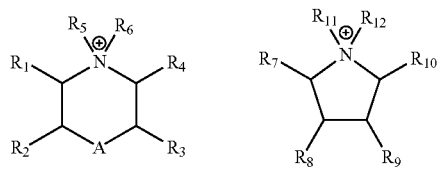

where A is a >$CR_{13}R_{14}$ group, a >C=O group, or an >O group, where $R_1$, $R_2$, $R_3$, $R_4$, $R_7$, $R_8$, $R_9$, and $R_{10}$ are each independently hydrogen, a hydroxyl group, or a $C_1$-$C_5$ hydrocarbon chain, where $R_{13}$ and $R_{14}$ are each independently hydrogen or a $C_1$-$C_5$ hydrocarbon chain, where $R_5$, $R_6$, $R_{11}$, and $R_{12}$ are each independently a $C_1$-$C_5$ hydrocarbon chain, and where one of the $R_5$ and $R_6$ groups can alternately be connected to one of the $R_{13}$ and $R_{14}$ groups to form a $C_1$-$C_5$ hydrocarbon linking moiety. The entire contents of U.S. Patent Application Publication No. 2013/0095030 are incorporated herein by reference.

U.S. Patent Application Publication No. 2013/0115163, the entire contents of which are hereby incorporated by reference herein, discloses that MSE framework-type molecular sieves can be synthesized using a structure directing agent comprising one or more of the following dications: 3-hydroxy-1-(4-(1-methylpiperidin-1-ium-1 yl)butyl)quinuclidin-1-ium, 3-hydroxy-1-(5-(1-methylpiperidin-1-ium-1-yl)pentyl) quinuclidin-1-ium, 1,1'-(butane-1,4-diyl)bis(1-methylpiperidin-1-ium), 1,1'-(pentane-1,5-diyl)bis(1-methylpiperidin-1-ium), 1,1'-(hexane-1,6-diyl)bis(1-methylpiperidin-1-ium), and 1,1'-((3as,6as)-octahydropentalene-2,5-diyl)bis(1-methylpiperidin-1-ium).

MSE framework-type molecular sieves have attracted interest as catalysts for fluid catalytic cracking (FCC) of hydrocarbon feeds since they generate high yields of propylene. However, this interest has been limited by the tendency for MSE framework-type to undergo rapid aging, particularly during catalyst regeneration. There is therefore interest in producing MSE framework-type molecular sieves with improved lifetime, especially in FCC catalytic applications.

SUMMARY OF THE INVENTION

According to the present invention, it has now been found that potassium, a source of alkali metal cations in most existing synthesis routes for MSE framework-type molecular sieves, is more strongly occluded in MSE materials than other framework-type materials and may be a factor in the aging characteristics of the molecular sieve. While not wishing to be bound by any theory of operation, it is believed that this residual potassium can be released during the in-situ steaming that occurs during FCC catalyst regeneration, and once released, can titrate acid sites of the molecular sieve, thereby effectively reducing the catalyst life. To obviate and/or reduce this issue, methods of reducing the level of occluded potassium in as-synthesized MSE framework-type molecular sieves have now been developed.

In one aspect, the invention can include a method for reducing the level of occluded alkali metal cations from an MSE-framework type molecular sieve, the method comprising: (a1) contacting an MSE framework-type molecular sieve containing a first amount of occluded potassium ions with a solution containing ammonium ions at a temperature of at least about 50° C. to ammonium-exchange at least part of the occluded potassium ions and produce a treated molecular sieve containing a second amount of occluded potassium ions, wherein the second amount is less than the first amount and preferably can be no more than about 0.1 wt % of the treated molecular sieve.

In a further aspect, the invention can include a method for reducing a level of occluded alkali metal cations from an MSE-framework type molecular sieve, the method comprising: (a2) contacting an MSE framework-type molecular sieve containing a first amount of occluded potassium ions with steam at a temperature of at least about 300° C. to produce a steamed molecular sieve; and (b2) contacting the steamed molecular sieve containing with a solution containing ammonium ions to ammonium-exchange at least part of the potassium ions in the steamed molecular sieve and produce a treated molecular sieve containing a second amount of occluded potassium ions, wherein the second amount is less than the first amount and preferably can be no more than about 0.1 wt % of the treated molecular sieve.

BRIEF DESCRIPTION OF THE DRAWINGS

FIG. 1 compares the powder X-ray diffraction data of the samples of Example 1 before and after steaming for about 16 hours at ~760° C. and ~900° C.

DETAILED DESCRIPTION OF THE EMBODIMENTS

Molecular sieves of the MSE framework-type, as described in the Atlas of Zeolite Framework Types, 6th edition, Elsevier, London, England (2007), have a 3-dimensional channel structure comprising one 12-membered ring channel system and two 10-membered ring channel systems. The channels of each system are believed to extend relatively perpendicular to the channels of the other systems, with the 12-ring channels being generally straight and the 10-ring channels being tortuous (sinusoidal). The 12-membered ring channels are believed to have cross-sectional dimensions of ~6.4 Å by ~6.8 Å, while the 10-membered ring channels are believed to have cross-sectional dimensions of ~5.2 Å by ~5.8 Å and ~5.2 Å by ~5.2 Å. Examples of MSE framework-type molecular sieves, as used herein, can include, but are not limited to, MCM-68 and UZM-35.

In its calcined form, MCM-68 can have an X-ray diffraction (XRD) pattern distinguishable from the patterns of other known as-synthesized and/or thermally treated crystalline materials, for example by the d-spacings/peak intensities listed in Table 1 below.

TABLE 1

| d (Å) | Relative Intensity [100 xI/Io] |
|---|---|
| 13.60 +/− 0.39 | S |
| 13.00 +/− 0.37 | VS |
| 10.92 +/− 0.31 | M |
| 10.10 +/− 0.29 | M |
| 9.18 +/− 0.26 | VS |
| 8.21 +/− 0.23 | W |
| 4.58 +/− 0.13 | W |
| 4.54 +/− 0.13 | W |
| 4.45 +/− 0.13 | VW-W |
| 4.32 +/− 0.12 | VW |
| 4.22 +/− 0.12 | VW |
| 4.10 +/− 0.12 | VS |
| 4.05 +/− 0.11 | M |
| 3.94 +/− 0.11 | M |
| 3.85 +/− 0.11 | M |
| 3.80 +/− 0.11 | VW |

TABLE 1-continued

| d (Å) | Relative Intensity [100 xI/Io] |
|---|---|
| 3.40 +/− 0.10 | W |
| 3.24 +/− 0.09 | W |
| 2.90 +/− 0.08 | VW |

The X-ray diffraction data reported herein were collected with a Panalytical X'Pert Pro diffraction system with an Xcelerator multichannel detector, equipped with a germanium solid state detector, using copper K-alpha radiation. The diffraction data were recorded by step-scanning at ~0.02° 2θ, where θ is the Bragg angle, and using an effective counting time of ~2 seconds for each step. The interplanar (d−) spacings were calculated in Angstrom units, and the relative intensities of the lines, I/Io, adjusted as percentages of the intensity of the strongest peak, Io (~100), above background, were derived with the use of Materials Data, Inc., Jade software peak search algorithm. The intensities were uncorrected for Lorentz and polarization effects. The relative intensities are given in terms of the symbols VS=very strong (>80-100%), S=strong (>60-80%), M=medium (>40-60%), W=weak (>20-40%), and VW=very weak (0-20%). In some embodiments, the peaks having intensities in the "very weak" category may be undetectable, whereas, in other embodiments, one or more (or indeed all) of the VW peak intensities may be detectable (thus non-zero and up to 20%). It should be understood that diffraction data listed for these samples as single lines/entries may consist of multiple overlapping lines/entries which, under certain conditions, such as differences in crystallographic changes, may appear as resolved or partially resolved. Typically, crystallographic changes can include minor changes in unit cell parameters and/or changes in crystal symmetry, without a corresponding change in the topological structure. These minor effects, including changes in relative intensities, can additionally or alternately occur as a result of various parametric effects, e.g., such as differences in cation content, framework composition, nature and degree of pore filling, crystal size and shape, preferred orientation, and thermal and/or hydrothermal history, inter alia.

The structure of MCM-68 is further discussed in U.S. Pat. No. 7,198,711 and in the Journal of Physical Chemistry B, 110, 2045 (2006).

MCM-68 has a chemical composition involving the molar relationship: $X_2O_3:(n)YO_2$, wherein X is a trivalent element, such as selected from at least one of aluminum, boron, gallium, iron, and chromium, preferably at least including aluminum; Y is a tetravalent element, such as selected from at least one of silicon, tin, titanium, vanadium, and germanium, preferably at least including silicon; and n is at least about 4, for example at least 7, such as from about 8 to about 100,000, and can typically be from about 10 to about 1000, for example from about 10 to about 100.

MCM-68 is generally thermally stable and, in the calcined form, can exhibit a relatively high surface area (e.g., about 660 m²/g, with a micropore volume of about 0.21 cc/g) and significant hydrocarbon sorption capacity as shown in Table 2.

TABLE 2

| Hydrocarbon, Conditions | MCM-68 Sorption Capacity |
| --- | --- |
| n-Hexane at ~75 torr, ~90° C. | ~10.8 wt % |
| Benzene at ~75 torr, ~30° C. | ~18.8 wt % |
| 2,2-Dimethylbutane at ~60 torr, ~120° C. | ~11.0 wt % |
| Mesitylene at ~2 torr, ~100° C. | ~3.3 wt % |

In its active, hydrogen form, MCM-68 can exhibit a relatively high acid activity, with an Alpha Value of about 900 to about 2000. Alpha Value is an approximate indication of the catalytic cracking activity of the catalyst compared to a standard catalyst, and it gives the relative rate constant (rate of normal hexane conversion per volume of catalyst per unit time). It is based on the activity of silica-alumina cracking catalyst taken as an Alpha of 1 (Rate Constant≈0.016 sec$^{-1}$). The Alpha Test is described in U.S. Pat. No. 3,354,078; and in the Journal of Catalysis, 4, 527 (1965); 6, 278 (1966); and 61, 395 (1980), each incorporated herein by reference as to that description. The experimental conditions of the test used herein include a constant temperature of about 538° C. and a variable flow rate, as described in detail in the Journal of Catalysis, 61, 395 (1980).

MCM-68 can be prepared from a reaction mixture comprising a source of water, a source of an oxide of a tetravalent element, Y, such as selected from at least one of silicon, tin, titanium, vanadium, and germanium, a source of an oxide of trivalent element, X, such as selected from at least one of aluminum, boron, gallium, iron, and chromium, a source of an alkali or alkaline earth metal, M, normally a source of potassium cations, together with a source of at least one organic structure directing agent, Q.

Preferred reaction mixtures can include a source of silicon oxide and a source of aluminum oxide. Suitable sources of silicon oxide can include, but are not necessarily limited to, colloidal silica, precipitated silica, potassium silicate, sodium silicate, fumed silica, and the like, as well as combinations thereof. Suitable sources of aluminum oxide can include, but are not necessarily limited to, hydrated aluminum oxides, such as boehmite, gibbsite, and pseudo-boehmite, especially gibbsite, as well as oxygen- and/or nitrogen-containing aluminum salts, such as aluminum nitrate, and the like, as well as combinations thereof.

Suitable organic directing agents, Q, can include, but are not necessarily limited to, N,N,N',N'-tetraethylbicyclo[2.2.2]oct-7-ene-2,3:5,6-dipyrrolidinium dications; N,N,N',N'-tetraalkylbicyclo[2.2.2]octane-2,3:5,6-dipyrrolidinium dications; 1,1-dialkyl-4-cyclohexyl-piperazin-1-ium cations; 1,1-dialkyl-4-alkylcyclohexylpiperazin-1-ium cations; tetraethyl-ammonium cations, and cations obeying one or more of the formulae:

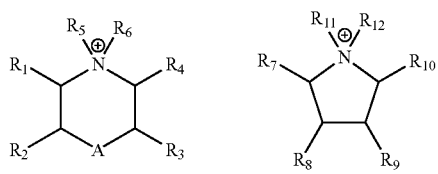

where A is a >$CR_{13}R_{14}$ group, a >C=O group, or an >O group, where $R_1$, $R_2$, $R_3$, $R_4$, $R_7$, $R_8$, $R_9$, and $R_{10}$ are each independently hydrogen, a hydroxyl group, or a $C_1$-$C_5$ hydrocarbon chain, where $R_{13}$ and $R_{14}$ are each independently hydrogen or a $C_1$-$C_5$ hydrocarbon chain, where $R_8$, $R_6$, $R_{11}$, and $R_{12}$ are each independently a $C_1$-$C_5$ hydrocarbon chain, and where one of the $R_5$ and $R_6$ groups can alternately be connected to one of the $R_{13}$ and $R_{14}$ groups to form a $C_1$-$C_5$ hydrocarbon linking moiety.

Other suitable cations for the synthesis of MCM-68 can additionally or alternately include one or more of the dications: 3-hydroxy-1-(4-(1-methylpiperidin-1-ium-1-yl)butyl)quinuclidin-1-ium, 3-hydroxy-1-(5-(1-methylpiperidin-1-ium-1-yl)pentyl)quinuclidin-1-ium, 1,1'-(butane-1,4-diyl)bis(1-methylpiperidin-1-ium), 1,1'-(pentane-1,5-diyl)bis(1-methyl-piperidin-1-ium), 1,1'-(hexane-1,6-diyl)bis(1-methylpiperidin-1-ium), and 1,1'-((3as,6as)-octahydropentalene-2,5-diyl)bis(1-methylpiperidin-1-ium).

The reaction mixture can also optionally comprise seeds of MSE framework type molecular sieve, such as MCM-68, for example, such that the weight ratio of seeds/$YO_2$ in the reaction mixture can be from about 0.001 to about 0.3, such as from about 0.001 to about 0.2.

Irrespective of the source of the structure directing agent(s), when the reaction mixture has been prepared, crystallization to produce the desired MCM-68 can be conducted under either static or stirred conditions in a suitable reactor vessel, such as for example, polypropylene jars or stainless steel autoclaves optionally lined with Teflon®, e.g., at a temperature from about 100° C. to about 200° C. for up to about 28 days, such as at a temperature from about 145° C. to about 175° C. for about 24 hours to about 170 hours. Thereafter, the crystals can advantageously be separated from the liquid and recovered.

The resultant as-synthesized MCM-68 can normally contain the structure directing agent(s) described above within its pore structure. The as-synthesized product may therefore be subjected to post-treatment to decompose and/or remove part or all of the organic structure directing agent Q used in its synthesis. This can be conveniently effected by thermal treatment, for example, in which the as-synthesized material is heated at a temperature of at least about 370° C. for at least 1 minute and generally not longer than 20 hours. While subatmospheric pressure can be employed for the thermal treatment, atmospheric pressure can be desired, typically for reasons of convenience. The thermal treatment can be performed at a temperature up to about 925° C. Additionally or alternatively, the organic structure directing agent Q can be removed/decomposed by treatment with ozone (see, e.g., Parikh et al., Microporous and Mesoporous Materials 76 (2004) 17-22).

The as-synthesized MCM-68 can additionally or alternately normally contain potassium cations transferred from the reaction mixture and occluded within the pore structure of molecular sieve. The amount of this occluded potassium can depend on many factors, including the composition of the reaction mixture and the framework aluminum content of the molecular sieve, but may be up to 5 wt %, for example up to about 4 wt %, up to about 3 wt %, up to about 2 wt %, or up to about 1 wt %, based on the weight of the as-synthesized molecular sieve. In most embodiments, the occluded potassium content can be more than about 0.1 wt %. for example at least about 0.2 wt %, at least about 0.25 wt %, at least about 0.3 wt %, at least about 0.4 wt %, or at least about 0.5 wt %, based on the weight of the as-synthesized molecular sieve.

According to one embodiment of the invention, the amount of occluded potassium in the as-synthesized MCM-68 can be reduced by contacting the molecular sieve with a solution containing ammonium ions at a temperature of at least about 50° C., for example at least about 60° C., at least about 70° C., about at least about 80° C., at least about 90°

C., or at least about 100° C. The concentration of ammonium ions in the solution used to contact the molecular sieve is not necessarily critical, but, in some embodiments, can be at least about 0.1M, for example at least about 0.25M, at least about 0.5M, at least about 0.75M, at least about 1M, at least about 1.25M, or at least about 1.5M. The time of the contacting with ammonium ion-containing solution can depend on a number of factors, including but not limited to the temperature and ammonium concentration of the solution, but, in certain embodiments, can be at least about 1 hour, for example at least about 2 hours, about at least about 3 hours, at least about 4 hours, at least about 8 hours, and/or up to about 168 hours, for example up to about 144 hours, up to about 120 hours, up to about 96 hours, up to about 72 hours, or up to about 48 hours. Any range of time within these values may be appropriate.

In particular, it has been found that treating the as-synthesized MCM-68 with a solution containing ammonium ions at a temperature of at least 50° C., at least part of the potassium ions occluded in the molecular sieve can be exchanged with ammonium ions. As a result, the treated molecular sieve can contain a lower concentration of occluded potassium ions than the untreated molecular sieve. Typically, the treated molecular sieve can contain no more than about 0.1 wt %, for example no more than about 0.08 wt %, no more than about 0.05 wt %, no more than about 0.04 wt %, or no more than about 0.02 wt % of occluded potassium ions.

In certain embodiment of the invention, the amount of occluded potassium in the as-synthesized MCM-68 can be reduced by (a) initially contacting the molecular sieve with steam at a temperature of at least about 300° C. to produce a steamed molecular sieve and then (b) contacting the steamed molecular sieve with a solution containing ammonium ions to ammonium-exchange at least part of the potassium ions in the steamed molecular sieve.

The initial contacting with steam can be conducted in an atmosphere of up to 100% steam, for example at least about 3% or at least about 10% steam, for a time, depending on the steam temperature and concentration, of at least about 1 hour, for example at least about 2 hours, at least about 3 hours, at least about 4 hours, at least about 8 hours, and/or up to about 168 hours, for example up to about 144 hours, up to about 120 hours, up to about 96 hours, up to about 72 hours, or up to about 48 hours. In some embodiments, the steam temperature can be at least about 350° C., for example at least about 400° C., at least about 450° C., or at least about 500° C., and/or less than about 1100° C., for example less than about 1000° C., less than about 900° C., less than about 800° C., or less than about 700° C., for instance to avoid loss of zeolite crystallinity. Any range of time and temperature within these values may be appropriate.

The subsequent contacting of the steamed molecular sieve with a solution containing ammonium ions can be conducted at any temperature above the freezing point of the solution but, in certain embodiments, can be conducted at a temperature of at least about 10° C., for example at least about 15° C., at least about 20° C., or at least about 25° C., but generally less than about 100° C., for example less than about 50° C. The concentration of ammonium ions in the solution used to contact the steamed molecular sieve is not necessarily critical, but, in some embodiments, can be at least about 0.1M, for example at least about 0.25M, at least about 0.5M, at least about 0.75M, at least about 1M, at least about 1.25M, or at least about 1.5M. The time of the contacting with ammonium ion-containing solution can depend on a number of factors, including but not limited to the temperature and ammonium concentration of the solution, but, in embodiments, can be at least about 1 hour, for example at least about 2 hours, at least about 3 hours, or at least about 4 hours, and/or up to about 72 hours, for example up to about 48 hours, up to about 24 hours, or up to about 16 hours. Any range of time within these values may be appropriate.

Typically, the molecular sieve resulting from the combined steaming/ammonium exchange can contain no more than about 0.1 wt %, for example no more than about 0.08 wt %, no more than about 0.05 wt %, no more than about 0.04 wt %, or no more than about 0.02 wt % of occluded potassium ions.

The above-mentioned treatments to reduce occluded potassium can normally be conducted after at least partial removal and/or decomposition of the organic structure directing agent from the as-synthesized MSE framework-type molecular sieve, which treatment(s) can advantageously result in a molecular sieve at least partly in an ammonium form. Thus, after such treatment(s), the molecular sieve can be converted to the active (hydrogen) form, for example by calcining at a temperature from about 25° C. to about 450° C. for a time of about 0.5 hours to about 48 hours. Alternately or in addition, the ammonium or hydrogen ions can be exchanged with other cations, particularly cations that can tailor the catalytic activity of the molecular sieve for certain hydrocarbon conversion reactions (e.g., rare earth elements and/or elements of Groups 3, 4, 5, 6, 7, 8, 9, 10, 11, 12, and/or 13 of the Periodic Table of the Elements).

The crystalline molecular sieve produced by the present process can be used to catalyze a wide variety of organic compound conversion processes including many of present commercial/industrial importance. Examples of chemical conversion processes effectively catalyzed by the crystalline material of this invention, by itself or in combination with one or more other catalytically active substances including other crystalline catalysts, can include those requiring a catalyst with acid activity. Specific examples can include, but are not limited to:

a) alkylation of aromatics with short chain ($C_2$-$C_6$) olefins, e.g., alkylation of ethylene or propylene with benzene to produce ethylbenzene or cumene respectively, in the gas or liquid phase, with reaction conditions optionally including one or more of a temperature from about 10° C. to about 250° C., a pressure from about 0 psig to about 500 psig (about 3.5 MPag), a total weight hourly space velocity (WHSV) from about 0.5 $hr^{-1}$ to about 100 $hr^{-1}$, and an aromatic/olefin mole ratio from about 0.1 to about 50;

b) alkylation of aromatics with long chain ($C_{10}$-$C_{20}$) olefins, in the gas or liquid phase, with reaction conditions optionally including one or more of a temperature from about 250° C. to about 500° C., a pressure from about 0 psig to 500 psig (about 3.5 MPag), a total WHSV from about 0.5 $hr^{-1}$ to about 50 $hr^{-1}$, and an aromatic/olefin mole ratio from about 1 to about 50;

c) transalkylation of aromatics, in gas or liquid phase, e.g., transalkylation of polyethylbenzenes and/or polyisopropylbenzenes with benzene to produce ethylbenzene and/or cumene respectively, with reaction conditions optionally including one or more of a temperature from about 100° C. to about 500° C., a pressure from about 1 psig (about 7 kPag) to about 500 psig (about 3.5 MPag), and a WHSV from about 1 $hr^{-1}$ to about 10,000 $hr^{-1}$;

d) disproportionation of alkylaromatics, e.g., disproportionation of toluene to produce xylenes, with reaction conditions optionally including one or more of a temperature from about 200° C. to about 760° C., a pressure from about 1 atm (about 0 psig) to about 60 atm (about 5.9 MPag), a WHSV from about 0.1 hr$^{-1}$ to about 20 hr$^{-1}$, and a hydrogen/hydrocarbon mole ratio from 0 (no added hydrogen) to about 50;

e) dealkylation of alkylaromatics, e.g., deethylation of ethylbenzene, with reaction conditions optionally including one or more of a temperature from about 200 to about 760° C., a pressure from about 1 atm (about 0 psig) to about 60 atm (about 5.9 MPag), a WHSV from about 0.1 hr$^{-1}$ to about 20 hr$^{-1}$, and a hydrogen to hydrocarbon mole ratio from 0 (no added hydrogen) to about 50;

f) isomerization of alkylaromatics, such as xylenes, with reaction conditions optionally including one or more of a temperature from about 200° C. to about 540° C., a pressure from about 100 kPaa to about 7 MPaa, a WHSV from 0.1 hr$^{-1}$ to about 50 hr$^{-1}$, and a hydrogen/hydrocarbon mole ratio from 0 (no added hydrogen) to about 10;

g) reaction of paraffins with aromatics, e.g., to form alkylaromatics and light gases, with reaction conditions optionally including one or more of a temperature from about 260° C. to about 375° C., a pressure from about 0 psig to about 1000 psig (about 6.9 MPag), a WHSV from about 0.5 hr$^{-1}$ to about 10 hr$^{-1}$, and a hydrogen/hydrocarbon mole ratio from 0 (no added hydrogen) to about 10;

h) paraffin isomerization to provide branched paraffins with reaction conditions optionally including one or more of a temperature from about 200° C. to about 315° C., a pressure from about 100 psig (about 690 kPag) to about 1000 psig (about 6.9 MPag), a WHSV from about 0.5 hr$^{-1}$ to about 10 hr$^{-1}$, and a hydrogen to hydrocarbon mole ratio from about 0.5 to about 10;

i) alkylation of iso-paraffins, such as isobutane, with olefins, with reaction conditions optionally including one or more of a temperature from about −20° C. to about 350° C., a pressure from about 0 psig to about 700 psig (about 4.9 MPag), and a total olefin WHSV from about 0.02 hr$^{-1}$ to about 10 hr$^{-1}$;

j) dewaxing of paraffinic feeds with reaction conditions optionally including one or more of a temperature from about 200° C. to about 450° C., a pressure from about 0 psig to about 1000 psig (about 6.9 MPag), a WHSV from about 0.2 to about 10 hr$^{-1}$, and a hydrogen/hydrocarbon mole ratio from about 0.5 to about 10;

k) cracking of hydrocarbons with reaction conditions optionally including one or more of a temperature from about 300° C. to about 700° C., a pressure from about 0.1 atm (about 10 kPag) to about 30 atm (about 3 MPag), and a WHSV from about 0.1 to about 20 hr$^{-1}$;

l) isomerization of olefins with reaction conditions optionally including one or more of a temperature from about 250° C. to about 750° C., an olefin partial pressure from about 30 kPa to about 300 kPa, and a WHSV from about 0.5 to about 500 hr$^{-1}$; and m) a hydrocarbon trap (e.g., pre-catalytic converter adsorbent) for cold start emissions in motor vehicles.

As described in U.S. Pat. No. 7,198,711, MCM-68 may be used as an additive component in conjunction with a conventional cracking catalyst, such as a large pore molecular sieve having a pore size greater than about 7 Angstroms.

As in the case of many catalysts, it may be desirable to incorporate the molecular sieve produced by the present process with another material resistant to the temperatures and other conditions employed in organic conversion processes. Such materials can include active and inactive materials and synthetic or naturally occurring zeolites, as well as inorganic materials such as clays, silica, and/or metal oxides such as alumina. The latter may be naturally occurring and/or in the form of gelatinous precipitates/gels including mixtures of silica and metal oxides. Use of a material in conjunction with the molecular sieve produced by the present process (i.e., combined therewith and/or present during synthesis of the new crystal), which is active, can tend to change the conversion capability and/or selectivity of the catalyst in certain organic conversion processes. Inactive materials can suitably tend to serve merely as diluents, e.g., to control the amount of conversion in a given process so that products can be obtained economically and orderly, for instance without employing too many other means for controlling the rate of reaction. These inventive materials may be incorporated into naturally occurring clays, e.g., bentonite and/or kaolin, to improve the crush strength of the catalyst under commercial operating conditions. Said materials (i.e., clays, oxides, etc.) can additionally or alternately function as binders for the catalyst. It can be desirable to provide a catalyst having good crush strength, because, in commercial use, it can often be desirable to prevent the catalyst from breaking down into powder-like materials (attrition). These (clay and/or oxide) binders have been employed normally only for the purpose of improving the crush strength of the catalyst.

Naturally occurring clays that can be composited with the molecular sieve produced by the present process can include, but are not limited to, the montmorillonite and kaolin families, which include the subbentonites and the kaolins commonly known as Dixie, McNamee, Ga., and Florida clays and/or others in which the main mineral constituent can be halloysite, kaolinite, dickite, nacrite, and/or anauxite. Such clays can be used in the raw state as originally mined and/or initially subjected to calcination, acid treatment, and/or chemical modification. Binders useful for compositing with the molecular sieve produced by the present process can additionally or alternatively include inorganic oxides, such as silica, zirconia, titania, magnesia, beryllia, alumina, and mixtures thereof.

Also additionally or alternately, the molecular sieve produced by the present process can be composited with a porous matrix material such as silica-alumina, silica-magnesia, silica-zirconia, silica-thoria, silica-beryllia, silica-titania, and/or ternary compositions such as silica-alumina-thoria, silica-alumina-zirconia silica-alumina-magnesia, and silica-magnesia-zirconia.

The relative proportions of finely divided crystalline molecular sieve material and inorganic oxide matrix vary widely, with the crystal content optionally ranging from about 1% to about 90% by weight and more usually, particularly when the composite is prepared in the form of beads or extrudates, ranging from about 2% to about 80% by weight of the composite.

Additionally or alternately, the invention can advantageously include one or more of the following embodiments.

Embodiment 1

A method for reducing a level of occluded alkali metal cations from an MSE-framework type molecular sieve, optionally comprising MCM-68, the method comprising: (a1) contacting an MSE framework-type molecular sieve containing a first amount of occluded potassium ions with a solution containing ammonium ions at a temperature of at least about 50° C. to ammonium-exchange at least part of the occluded potassium ions and produce a treated molecular sieve containing a second amount of occluded potassium ions, wherein the second amount is less than the first amount.

Embodiment 2

A method for reducing a level of occluded alkali metal cations from an MSE-framework type molecular sieve, optionally comprising MCM-68, the method comprising: (a2) contacting an MSE framework-type molecular sieve containing a first amount of occluded potassium ions with steam at a temperature of at least 300° C. to produce a steamed molecular sieve; and (b2) contacting the steamed molecular sieve with a solution containing ammonium ions to ammonium-exchange at least part of the potassium ions in the steamed molecular sieve thereby producing a treated molecular sieve containing a second amount of occluded potassium ions, wherein the second amount is less than the first amount.

Embodiment 3

The method of any one of the previous embodiments, wherein the MSE framework-type molecular sieve comprises an aluminosilicate, for example having a silicon to aluminum ratio of at least about 7.

Embodiment 4

The method of any one of the previous embodiments, wherein the first amount of occluded potassium ions at least about 0.25 wt % potassium by weight of the molecular sieve.

Embodiment 5

The method of any one of the previous embodiments, wherein the treated molecular sieve comprises more than about 0.10 wt % potassium.

Embodiment 6

The method of any one of embodiments 1 and 3-5, further comprising: (b1) crystallizing a reaction mixture comprising a source of water, a source of an oxide of a tetravalent element, Y, a source of a trivalent element, X, a source of potassium and a source of organic structure directing agent effective to direct the crystallization of an MSE framework-type molecular sieve from the reaction mixture; (c1) recovering crystals of MSE framework-type molecular sieve from the reaction mixture; and (d1) supplying at least part of the recovered crystals or a product thereof to the contacting (a1).

Embodiment 7

The method of embodiment 6, further comprising: (e1) removing at least part of the organic structure directing agent contained by the recovered crystals prior to supplying the crystals to the contacting (a1).

Embodiment 8

The method of any one of embodiments 1 and 3-7, further comprising: (f1) heating the treated molecular sieve to convert at least part of the exchanged ammonium ions to hydrogen ions.

Embodiment 9

The method of any one of embodiments 2-8, wherein the contacting (b2) is conducted with a solution containing ammonium ions at a temperature of at least about 10° C.

Embodiment 10

The method of any one of embodiments 2-9, further comprising: (c2) crystallizing a reaction mixture comprising a source of water, a source of an oxide of a tetravalent element, Y, a source of a trivalent element, X, a source of potassium and a source of organic structure directing agent effective to direct the crystallization of an MSE framework-type molecular sieve from the reaction mixture; (d2) recovering crystals of MSE framework-type molecular sieve from the reaction mixture; and (e2) supplying at least part of the recovered crystals or a product thereof to the contacting (a2).

Embodiment 11

The method of embodiment 10, further comprising: (f2) removing at least part of the organic structure directing agent contained by the recovered crystals prior to supplying the crystals to the contacting (a2).

Embodiment 12

The process of any one of embodiments 2-11, further comprising: (g2) heating the treated molecular sieve to convert at least part of the exchanged ammonium ions to hydrogen ions.

The invention will now be more particularly described with reference to the following non-limiting Examples and the accompanying drawings.

EXAMPLES

Example 1

A sample of MCM-68 having a Si/Al atomic ratio of ~21 was prepared using N,N-dimethyl-4-cyclohexylpiperazinum cations as the structure directing agent from a reaction mixture having the following molar composition ratios:

$SiO_2/Al_2O_3 \approx 80.2$;
$K/SiO_2 \approx 0.33$;
$SDA/SiO_2 \approx 0.17$;
$OH^-/SiO_2 \approx 0.50$; and
$H_2O/SiO_2 \approx 25.6$.

Details of the MCM-68 synthesis are as follows. In one container, about 244 grams of $Al(NO_3)_3$ was dissolved in ~1.16 kg water. Stirring was continued until all of the salt appeared to be visually dissolved in the water. In a second container, about 3.15 kg of KASIL-6™ (potassium silicate) and about 2.44 kg of LUDOX AS-30™ (colloidal silica) were added to ~4.1 kg of water. The mixture was stirred until it appeared to be homogeneous. The $Al(NO_3)_3$ was slowly added to an agitated silicate solution. About 3.87 kg of a ~29 wt % solution of N,N-dimethyl-4-cyclohexyl-piperazinum hydroxide was then added to the aluminosilicate mixture and stirred for an additional ~10-15 minutes. About 37.1 g of MCM-68 seed crystals were added to the aluminosilicate mixture and stirred for ~15-20 minutes, for example to make sure that the mixture was roughly homogeneous. The mixture was then transferred to a stirred ~5-gallon autoclave. The mixture was stirred at ~250 rpm, and the resultant gel was heated to about 160° C. (about 320° F.) for ~3 days.

After ~3 days, the material was flocculated, vacuum filtered, washed with ~3 volumes of water, and dried in a forced draft oven. The X-ray diffraction pattern of resulting product seemed to indicate that the resultant crystal was indeed MCM-68. Elemental analysis showed the material to have a bulk Si/Al ratio of about 21.

The as-synthesized zeolite was purported to contain ~0.70 wt % K and was calcined in a muffle furnace by heating in a nitrogen stream from ambient temperature (~20-25° C.) to ~400° C. over roughly a 2-hr period, maintaining this temperature for ~15 minutes, switching the gas stream to air, increasing the temperature from ~400° C. to ~600° C., again over roughly a 2-hr period, maintaining the temperature at ~600° C. for about 2 hours, and then allowing the furnace to cool to ambient conditions (~20-25° C.). Ion exchange was then carried out on the calcined zeolite by adding the zeolite to a ~10-fold mass of deionized water and adding approximately an equal mass of ammonium nitrate, which appeared to create a ~1.1M $NH_4NO_3$ solution. The slurry was then placed in a polypropylene bottle and heated within a steambox overnight (~8-16 hours) at ~98° C. The zeolite was then filtered and washed with at least ~300 mL deionized water. This ion-exchange procedure was performed twice.

The zeolite was then converted to the acidic form by calcining the zeolite from ambient conditions (~20-25° C.) to ~500° C., over a ~2-hour period, maintaining that temperature for ~4 hours, and then allowing the furnace to cool to near-ambient conditions. About 4 g samples of the zeolite from this parent batch were then steamed at temperatures of ~371° C., ~427° C., ~538° C., ~760° C., and ~900° C. In each steaming test, the zeolite powder was loaded into a vertical quartz-tube reactor and was heated under a flow of nitrogen gas at ~5° C./min. When the desired temperature was reached, water was dripped from the top of the reactor into the heated bed at a rate of ~5 $cm^3$/hr. Each sample was then steamed for ~16 hours. After each sample was cooled, powder XRD data were collected on the samples and the steamed zeolites were submitted for nitrogen physisorption and alpha testing.

The powder XRD data are shown in FIG. 1 and appeared to demonstrate that the low angle peaks in the patterns of MCM-68 gain intensity after steam treatment at ~760° C. This effect was generally observed in the powder diffraction patterns of zeolites during the removal of extra-framework species whether by calcination or by dehydration. FIG. 1 also appears to show, after steaming at ~900° C., a significant loss in the crystallinity of the sample. Nonetheless, even at these relatively harsh conditions, the sample still appeared to retain slightly more than half of its original microporosity.

The BET surface area, micropore volume, and alpha value results for each of the steamed samples are shown in Table 3. In one case, multiple alpha tests were run when the measured alpha was less than ~10—this was indicated by two numbers in parentheses.

TABLE 3

| Steam Temperature ° C. | BET Surf Area ($m^2$/g) | Micropore Vol (cc/g) | Alpha |
| --- | --- | --- | --- |
| Unsteamed | ~549 | ~0.21 | ~640 |
| ~371 | ~560 | ~0.20 | ~650 |
| ~427 | ~571 | ~0.20 | ~410 |
| ~538 | ~527 | ~0.19 | ~110 |
| ~760 | ~509 | ~0.19 | ~25, ~32 |
| ~900 | ~306 | ~0.12 | <~10 (~9, ~9) |

As can be seen from Table 3, only minor decreases in the micropore volume appeared to occur in the steam treatments up to ~760° C. (from ~0.21 cc/g to ~0.19 cc/g). This observation is believed to be consistent with maintenance of the crystallinity in the powder XRD patterns up to ~760° C. Without being bound by theory, the relatively small decreases may be due to the presence of increasing concentrations of extra-framework aluminum that can occupy space within the micropores. $^{27}$Al NMR appeared to show the expected increase in non-framework aluminum with increasing temperature of the steam treatment. Even after steaming at ~900° C., slightly more than half of the micropore volume of the MCM-68 was maintained (~0.12 cc/g). The loss in micropore volume appeared to be consistent with the loss in intensity observed in the powder XRD pattern (FIG. 1). The parent sample of MCM-68 was measured to possess an alpha value of ~640. For a steaming temperature of ~371° C., virtually no change in the alpha value was observed. Above ~371° C., a relatively monotonic decrease in alpha was observed with increasing temperature: alpha values of ~410, ~110, and ~25 at ~427, ~538, and ~760° C., respectively. At ~900° C., the alpha value was less than ~10 (two measurements produced alpha values of ~9 each). These data collectively appear to demonstrate that the MCM-68 possessed robust hydrothermal stability.

After the steam treatment of each sample, half of each sample was washed with a solution of ~1.1M ammonium nitrate. This was carried out using the same proportion of solution to zeolite as described above for the ammonium exchange of the parent zeolite. The purpose of this treatment was to determine whether any potassium, having been liberated during the steaming, could be removed from the zeolite. If so, then this could enhance the lifetime of the zeolite in subsequent FCC testing. Each sample (both before and after each ion-exchange) was then submitted for elemental analyses for Si, Al, and K. The results of the elemental analyses are shown in Table 4, in which the samples that were washed with ammonium nitrate after the steam treatment included the descriptor "N" after the steam temperature. Surprisingly, none of the samples appeared to have appreciable potassium after each treatment. This was unexpected, because initial work on MCM-68 had shown that the potassium could not be removed completely by ion-exchange.

TABLE 4

| Steam Temp (° C.) | Wt % $Al_2O_3$ | Wt % $SiO_2$ | Wt % K | Atomic Si/Al |
| --- | --- | --- | --- | --- |
| ~371 | ~3.64 | ~91.4 | ~0.02 | ~21.3 |
| ~427 | ~3.61 | ~91.3 | ~0.02 | ~21.5 |
| ~538 | ~3.67 | ~92.9 | ~0.02 | ~21.5 |
| ~760 | ~3.67 | ~93.2 | ~0.02 | ~21.6 |
| ~900 | ~3.70 | ~93.5 | ~0.02 | ~21.5 |
| ~371N | ~3.10 | ~87.1 | <~0.01 | ~23.9 |
| ~427N | ~3.06 | ~87.0 | <~0.01 | ~24.1 |
| ~538N | ~3.46 | ~89.9 | ~0.012 | ~22.1 |
| ~760N | ~3.58 | ~92.5 | <~0.01 | ~21.9 |
| ~900N | ~3.72 | ~93.5 | ~0.02 | ~21.3 |
| Parent Sample Before Calcination | ~3.12 | ~76.8 | ~0.70 | ~20.9 |
| Parent Sample After Calcination/Exchange | ~3.31 | ~82.8 | ~0.02 | ~21.2 |

Table 4 also appears to show that, for samples that have been steamed without a subsequent wash in the ammonium nitrate solution, the bulk Si/Al ratios appeared to remain constant within the experimental limits of the measurements. However, after the ammonium washes, there seemed to be some loss in the aluminum content for the samples with steam treatments at lower temperatures. Although the reason for this result may not be fully understood, it has been speculated that this may be because dealumination at lower temperatures can produce discrete aluminum species that can be easily removed with a mildly acidic wash. At higher steaming temperatures, the extra-framework aluminum/alumina may sinter into species not as easily removed by such treatment(s).

Example 2

A sample of MCM-68 having a Si/Al atomic ratio of ~8 was prepared using 4-ethyl-4-methylmorpholium cations as the structure directing agent according to the following procedure.

About 8.68 g of KOH (88%) pellets were dissolved in ~36.4 g of deionized water. While the KOH solution was still hot, about 0.54 g of Al(OH)$_3$ dried gel was added, and the solution was stirred until the Al(OH)$_3$ visually appeared to completely dissolve. About 83.0 g of ~0.98 mmol/g 4-ethyl-4-methylmorpholium hydroxide was then added to the aluminate solution. About 40.7 g of Ludox AS-40™ and about 0.72 g of MCM-68 seeds were then sequentially added to the solution (see Example 1). The gel was then charged to a ~300-mL overhead-stirred autoclave. The mixture was stirred at ~200 rpm and heated to ~160° C. (~320° F.) for ~4 days, after which the crystalline product was recovered by vacuum filtration, washed with ~500 mL of deionized water, and dried in an oven at ~100° C. The X-ray diffraction pattern of resulting product appeared to indicate that the resultant crystal was indeed MCM-68.

The resultant zeolite crystal was calcined, and then four separate samples were ion exchanged in the same way as in Example 1, except for one sample in which ion exchange was conducted at room temperature (~20-25° C.) for ~24 hours. For the other three samples, the ion exchange was conducted at room temperature (~20-25° C.) for ~7 days, at ~50° C. for ~24 hours, and at ~70° C. for ~24 hours, respectively. The results are shown in Table 5.

TABLE 5

| Exchange Temp | Exchange Time | Wt % SiO$_2$ | Wt % Al$_2$O$_3$ | Atomic Si/Al | Wt % K |
|---|---|---|---|---|---|
| Ambient | ~24 hrs | ~76.5 | ~7.97 | ~8.15 | ~0.55 |
| Ambient | ~7 days | ~77.8 | ~8.07 | ~8.18 | ~0.47 |
| ~50° C. | ~24 hrs | ~74.9 | ~7.69 | ~8.27 | ~0.43 |
| ~75° C. | ~24 hrs | ~75.4 | ~7.86 | ~8.15 | ~0.38 |

As shown in Table 5, the potassium level of the sample exchanged at room temperature for ~24 hours was ~0.55% and, for the sample exchanged at room temperature for ~7 days, was ~0.47%. At these lower temperatures, time appeared to a very little effect on the exchange of the zeolite. As the temperature was increased, however, there appeared to be a monotonically decreasing level of potassium, compared to that of the samples exchanged at room temperature.

Example 3

A sample of MCM-68 having a Si/Al atomic ratio of ~12.3 was prepared using 1-butyl-1-methyl-piperidinium cations as the structure directing agent The zeolite was calcined in the same way as in Example 1, and then three separate samples were ion exchanged again in the same way as in Example 1, except that the ion exchange was conducted for ~24 hours at ~98° C. (exchange conducted twice), ~115° C., and ~160° C., respectively. The results are shown in Table 6.

TABLE 6

| Ion Exchange Temp, ° C. | Exchange Time | Atomic Si/Al | Wt % K |
|---|---|---|---|
| Parent (before organic removal/decomposition) | N/A | ~12.3 | ~3.62 |
| ~98 | ~24 hrs (twice) | ~12.1 | ~0.90 |
| ~115 | ~24 hrs | ~12.2 | ~0.25 |
| ~160 | ~24 hrs | ~11.5 | ~0.12 |

As shown in Table 6, it was not possible to remove all of the potassium from the product of Example 3 even after using exchange temperatures up to ~160° C. for ~24 hours, although a gradual reduction in the potassium concentration was observed as the temperature of the exchange increased. Note the contrast with the case of MCM-68 with higher Si/Al (~21) in Example 1, in which all of the potassium was removed at ~100° C. The potassium cation therefore appeared to be more tightly bound in the product of Example 3 than in the same zeolite with a higher Si/Al ratio.

Example 4

The results of steaming studies on another MCM-68 sample produced with a Si/Al atomic ratio of ~13 are shown in Table 7. All steaming tests were conducted for ~4 hours at the temperatures listed below.

TABLE 7

| Steaming Temp., ° C. | BET Surface Area (m$^2$/g) | Micropore Volume (cc/g) | Alpha |
|---|---|---|---|
| Unsteamed | ~547 | ~0.18 | ~730 |
| ~371 | ~515 | ~0.16 | ~500 |
| ~538 | ~507 | ~0.16 | ~73 |
| ~649 | ~463 | ~0.15 | <~10 (~5) |
| ~815 | ~421 | ~0.14 | <~10 (~3) |
| ~982 | ~22 | ~0.00 | ~0 |

Comparing the results in Table 7 with those in Table 3, it can be seen that, although the more aluminous sample of Example 4 started with a somewhat higher alpha value before steaming (~730 versus ~640), its alpha value appeared to decrease much more quickly with temperature, even though the steaming time was ~4 times shorter (~4 hours versus ~16 hours) than in Example 1. For example, between ~538° C. and ~649° C., the alpha value decreased from ~73 to ~5. In the MCM-68 sample with Si/Al≈21 (Example 1), the alpha value was ~110 and ~25 at ~538° C. and ~760° C., respectively. The powder XRD patterns of the MCM-68 (Si/Al 13) of Example 4 appeared to remain sharp up to a steaming temperature of ~815° C., thus making it unlikely for the drops in alpha value to be due to a reduction in the degree of crystallinity. Without being bound by theory, the more precipitous drop in the alpha value in the zeolite of Example 4 is believed to be due to the titration of acid sites by the potassium cations that become liberated during zeolite dealumination. In the case of MCM-68 (Si/Al≈21) in Example 1, the $^{27}$Al NMR data appear to show a pronounced degree of dealumination between ~538° C. and ~760° C.

This is within the range in which the dramatic drop in alpha value was seen for the MCM-68 (Si/Al≈13) of Example 4.

Example 5

A sample of MCM-68 having a Si/Al atomic ratio of ~12 was prepared using 1-butyl-1-methyl-piperidinium cations as the structure directing agent. The following gel composition molar ratios were calculated based upon the weights of the reagents used in the procedure shown below:

$SiO_2/Al_2O_3$≈48.0
$K/SiO_2$≈0.30
$SDA/SiO_2$≈0.30
$OH^-/SiO_2$≈0.60; and
$H_2O/SiO_2$≈22.3.

About 544 grams of KOH pellets were dissolved in 2.8 kg of water. While the KOH solution was still hot, ~99.3 g of Al(OH)$_3$ dried gel was added and the solution stirred until the Al(OH)$_3$ was completely dissolved. About 7.3 kg of ~20% 1-butyl-1-methyl piperidinium hydroxide to the aluminate solution and the resultant mixture stirred for ~5 minutes. About 67.0 grams of MCM-68 seeds were then added to the aluminate mixture, stirring for ~5 minutes to disperse the seeds. About 4.23 kg of Ludox HS-40 was then added, and the gel was mixed for another ~30 minutes, prior to charging to a ~5-gallon stirred autoclave. The mixture was stirred at ~250 rpm and heated to ~160° C. (~320° F.) for about 2 days, after which the crystal was flocculated, vacuum filtered, washed with ~3 volumes of water, and dried in a forced draft oven. The X-ray diffraction pattern of resulting product indicated that the crystal was MCM-68.

The as-synthesized zeolite contained ~0.9 wt % K. The zeolite was calcined and then ion exchanged in the same way as in Example 1, with the ion exchange being conducted at ~98° C. for ~12 hours. The steaming studies of Example 4 were repeated on the ion exchanged samples; the results are shown in Table 8.

TABLE 8

| Steaming Temp. ° C. | BET Surface Area (m²/g) | Micropore Volume (cc/g) | Alpha | Alpha w/ NH₄-exch. after steaming |
|---|---|---|---|---|
| Unsteamed | ~448 | ~0.17 | — | — |
| ~371 | ~417 | ~0.15 | ~850 | — |
| ~427 | ~477 | ~0.18 | ~580 | — |
| ~538 | ~411 | ~0.15 | ~34 | ~540, ~530 |
| ~760 | ~339 | ~0.13 | <~10 (~3) | ~73, ~68 |
| ~900 | ~10 | ~0.00 | <~10 (~1) | ~0 |

As shown in Table 8, the alpha value appeared to fall much more precipitously with temperature in the case of the Example 5 samples than for the MCM-68 with Si/Al≈21 in Example 1 (Table 1). Note that the alpha values were measured as ~34 and ~3 after steaming at temperatures of ~538° C. and ~760° C., respectively. After steaming at ~900° C., the MCM-68 with low Si/Al (~12) appeared to have been largely amorphitized (as shown by powder XRD).

We speculated that, if these samples were ammonium-exchanged subsequent to the steaming, then the liberated potassium cations that appeared to titrate the acid sites could be potentially removed. Furthermore, since dealumination typically produces a framework with lower negative charge density, it could be easier to remove any extra-framework cations that can compensate the charge of framework aluminum and reside in the wall sites. Thus ammonium ion exchange was conducted (at ~98° C. in ~1M ammonium nitrate solution overnight, or for about 8-16 hours) on the samples that had been steamed at ~538+° C. The results are also listed in Table 8 and show that, after the post-steaming ion exchange, the alpha value increased from ~34 to ~530 for the sample steamed at ~538° C., and from ~3 to ~68 for the sample steamed at ~760° C. For the same steaming temperatures, these alpha values represent an even greater activity than those observed for the MCM-68 with Si/Al≈21. By performing an additional ion-exchange after the steam treatment, alpha was increased by more than an order of magnitude.

Example 6 (Comparative)

For comparative purposes, steaming studies were also performed on ZSM-5 with Si/Al ratio of ~13 prepared with n-propylamine as the structure directing agent. Steaming studies were performed on the ZSM-5 sample after calcination and ammonium-exchange to remove substantially all sodium. As in the case of the MCM-68, the ZSM-5 sample was found to maintain its crystallinity after steam treatment at ~760° C., but, after steaming at ~900° C., substantial broadening appeared in the powder XRD pattern. Table 9 shows the alpha values of the ZSM-5 sample after steam treatment.

TABLE 9

| Steam Temperature, ° C. | Alpha |
|---|---|
| ~760 | <~10 (~6) |
| ~900 | <~10 (~2) |

Comparing the results of Tables 8 and 9, it can be seen that, for materials possessing similar Si/Al ratios (~12 and ~13) that have been completely exchanged (which, in the case of MCM-68, included post-steaming ammonium exchange), MCM-68 steamed at ~760° C. possessed an alpha value an order of magnitude greater than that of ZSM-5.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A method for reducing a level of occluded alkali metal cations from an MSE-framework type molecular sieve, the method comprising:
    (a1) contacting an MSE framework-type molecular sieve containing a first amount of occluded potassium ions with a solution containing ammonium ions at a temperature of at least about 50° C. to ammonium-exchange at least part of the occluded potassium ions and produce a treated molecular sieve containing a second amount of occluded potassium ions, wherein the second amount is less than the first amount; and
    exchanging the treated molecular sieve with cations of a rare earth element.

2. The method of claim 1, wherein the MSE framework-type molecular sieve comprises MCM-68.

3. The method of claim 1, wherein the MSE framework-type molecular sieve comprises an aluminosilicate.

4. The method of claim 3, wherein the MSE framework-type molecular sieve has a silicon to aluminum atomic ratio in the range of from about 21 to about 1000.

5. The method of claim 1, wherein the first amount of occluded potassium ions is at least about 0.25 wt % potassium by weight of the molecular sieve.

6. The method of claim 1, wherein the second amount of occluded potassium ions in the treated molecular sieve is no more than about 0.10 wt % potassium.

7. The method of claim 1, further comprising:
(b1) crystallizing a reaction mixture comprising a source of water, a source of an oxide of a tetravalent element, Y, a source of a trivalent element, X, a source of potassium and a source of organic structure directing agent effective to direct the crystallization of an MSE framework-type molecular sieve from the reaction mixture;
(c1) recovering crystals of MSE framework-type molecular sieve from the reaction mixture; and
(d1) supplying at least part of the recovered crystals or a product thereof to the contacting (a1).

8. The method of claim 7, further comprising:
(e1) removing at least part of the organic structure directing agent contained by the recovered crystals prior to supplying the crystals to the contacting (a1).

9. The method of claim 7, further comprising:
(f1) heating the treated molecular sieve to convert at least part of the exchanged ammonium ions to hydrogen ions.

10. The method of claim 1, wherein the treated molecular sieve is converted to a hydrogen form prior to exchanging with the cations of the rare earth element.

11. A method for reducing a level of occluded alkali metal cations from an MSE-framework type molecular sieve, the method comprising:
(a2) contacting an MSE framework-type molecular sieve containing a first amount of occluded potassium ions with steam at a temperature of at least about 300° C. to produce a steamed molecular sieve; and
(b2) contacting the steamed molecular sieve with a solution containing ammonium ions to ammonium-exchange at least part of the potassium ions in the steamed molecular sieve thereby producing a treated molecular sieve containing a second amount of occluded potassium ions, wherein the second amount is less than the first amount; and
exchanging the treated molecular sieve with cations of a rare earth element.

12. The method of claim 11, wherein the contacting (b2) is conducted with a solution containing ammonium ions at a temperature of at least about 10° C.

13. The method of claim 11, wherein the MSE framework-type molecular sieve comprises an aluminosilicate.

14. The method of claim 13, wherein the MSE framework-type molecular sieve has a silicon to aluminum atomic ratio of at least about 7.

15. The method of claim 11, wherein the first amount of occluded potassium ions in the molecular sieve is at least about 0.25 wt % potassium.

16. The method of claim 11, wherein the second amount of occluded potassium ions in the treated molecular sieve is less than about 0.10 wt % potassium.

17. The method of claim 11, further comprising:
(c2) crystallizing a reaction mixture comprising a source of water, a source of an oxide of a tetravalent element, Y, a source of a trivalent element, X, a source of potassium and a source of organic structure directing agent effective to direct the crystallization of an MSE framework-type molecular sieve from the reaction mixture;
(d2) recovering crystals of MSE framework-type molecular sieve from the reaction mixture; and
(e2) supplying at least part of the recovered crystals or a product thereof to the contacting (a2).

18. The method of claim 17, further comprising:
(f2) removing at least part of the organic structure directing agent contained by the recovered crystals prior to supplying the crystals to the contacting (a2).

19. The process of claim 17, further comprising:
(g2) heating the treated molecular sieve to convert at least part of the exchanged ammonium ions to hydrogen ions.

20. The method of claim 11, wherein the treated molecular sieve is converted to a hydrogen form prior to exchanging with the cations of the rare earth element.

* * * * *